United States Patent [19]

Fiege et al.

[11] Patent Number: 4,824,975
[45] Date of Patent: Apr. 25, 1989

[54] PROCESS FOR THE PREPARATION OF OXETANE-3-CARBOXYLIC ACIDS

[75] Inventors: Helmut Fiege, Leverkusen; Manfred Jautelat, Burscheid; Dieter Arlt, Cologne, all of Fed. Rep. of Germany

[73] Assignee: Bayer Aktiengesellschaft, Leverkusen, Fed. Rep. of Germany

[21] Appl. No.: 49,749

[22] Filed: May 13, 1987

[30] Foreign Application Priority Data

May 30, 1986 [DE] Fed. Rep. of Germany ....... 3618135

[51] Int. Cl.$^4$ .................. C00F 305/04; C00F 305/08
[52] U.S. Cl. .................. 549/511; 549/510; 71/88
[58] Field of Search ................ 549/510, 511

[56] References Cited

U.S. PATENT DOCUMENTS 4,599,446 7/1986 Kiyoura .......................... 562/527

FOREIGN PATENT DOCUMENTS 1907117 9/1970 Fed. Rep. of Germany .

OTHER PUBLICATIONS

Carl R. Noller, Chemistry of Organic Compounds (1965), p. 413.
Chemical Abstracts, 88:136,144z; 96:180978p.

Primary Examiner—Glennon H. Hollrah
Assistant Examiner—Mark W. Russell
Attorney, Agent, or Firm—Sprung Horn Kramer & Woods

[57] ABSTRACT

A process for the preparation of an oxetane-3-carboxylic acid of the formula

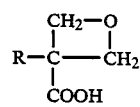

in which R represents hydrogen, alkyl, cycloalkyl or optionally substitute phenyl, comprising reacting a 3-hydroxymethyl-oxetane of the formula

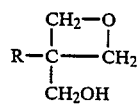

with oxygen in an aqueous alkaline medium at a temperature between about 0° C. and the boiling point of the reaction mixture on a palladium and/or platinum catalyst. The product is an intermediate for known fungicides and herbicides.

8 Claims, No Drawings

PROCESS FOR THE PREPARATION OF OXETANE-3-CARBOXYLIC ACIDS

The invention relates to a new process for the preparation of oxetane-3-carboxylic acids, some of which are known and can be used as intermediates for the synthesis of substances having a fungicidal or herbicidal activity.

It is already known that 3-alkyloxetane-3-carboxylic acids can be prepared starting from 3-alkyl-3-hydroxymethyl-oxetanes (cf. German Patent Specification No. 1,907,117). In the known process, 3-alkyl-3-hydroxymethyl-oxetanes are dehydrogenated in the liquid phase in the presence of catalysts containing copper/chromium/barium, at temperatures between 190° and 270° C. The 3-alkyl-oxetane-3-carboxylic acid esters obtained, which contain, as alcohol component, the 3-alkyl-3-hydroxymethyl-oxetane employed as starting material, are saponified to the 3-alkyl-oxetane-3-carboxylic acids in a further reaction step. This process has the disadvantages that it is a multistage synthesis and the 3-alkyl-oxetane-3-carboxylic acids desired can only be obtained in low yield and as a mixture with other products.

It has now been found that oxetane-3-carboxylic acids of the formula

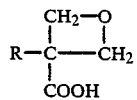
(I)

in which R represents hydrogen, alkyl, cycloalkyl or optionally substituted phenyl, can be prepared by reacting 3-hydroxymethyl-oxetanes of the formula

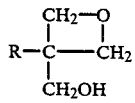
(II)

in which R has the abovementioned meaning, with an oxygen-containing gas, e.g. oxygen or air, in aqueous alkaline medium at temperatures between 0° C. and the boiling point of the reaction mixture on a palladium and/or platinum catalyst, if appropriate in the presence of an activator, and subsequently acidifying, if appropriate.

The course of the process according to the invention can be described as extremely surprising, since the chemical oxidation of 3-hydroxymethyl-oxetanes had hitherto not been described, apart from a thermal dehydrogenation. With regard to the known prior art, it could not have been presumed that oxetane-3-carboxylic acids of the formula (I) could be prepared directly in a single-stage reaction an oxidation of 3-hydroxymethyl-oxetanes.

The process according to the invention is distinguished by a number of advantages. Thus, the starting materials required are available easily and in large amounts. Furthermore, the necessary oxidants and other reaction components are also inexpensive and easy to handle. It is particularly advantageous that the desired products are produced in very high yield and excellent purity, so that further distillation purification of the thermally labile oxetane-3-carboxylic acids, which tend towards polymerization, is, in general, no longer necessary.

If 3-methyl-3-hydroxymethyloxetane is used as starting material, oxygen as oxidant, palladium and activated charcoal, with addition of bismuth nitrate, as catalyst, aqueous sodium hydroxide solution as reaction medium, and dilute aqueous sulphuric acid for acidification, then the course of the process according to invention may be illustrated by the following equation:

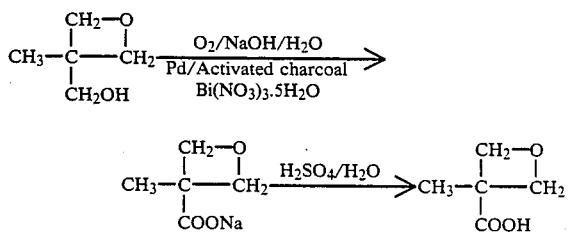

The 3-hydroxymethyl-oxetanes required as starting materials in the process according to the invention are generally defined by the formula (II). In this formula, R preferably represents hydrogen, alkyl having 1 to 12 carbon atoms, and cycloalkyl having 3 to 8 carbon atoms, or phenyl which is optionally substituted by halogen and/or alkyl having 1 to 6 carbon atoms.

Particularly preferred substances of the formula (II) are those in which R represents hydrogen, alkyl having 1 to 8 carbon atoms, particularly having 1 to 6 carbon atoms, cycloalkyl having 3 to 6 carbon atoms, or phenyl which is optionally substituted by fluorine, chlorine, bromine and/or alkyl having 1 to 4 carbon atoms.

The following may be mentioned as examples of 3-hydroxymethyl-oxetanes of the formula (II): 3-methyl-3-hydroxymethyl-oxetane, 3-ethyl-3-hydroxymethyl-oxetane, 3-propyl-3-hydroxymethyl-oxetane, 3-isopropyl-3-hydroxymethyl-oxetane and 3-butyl-3-hydroxymethyl-oxetane, 3-hydroxymethyl-oxetane, 3-phenyl-3-hydroxymethyl-oxetane, 3-cyclohexyl-3-hydroxymethyl-oxetane and 3-(4-chlorophenyl)-3-hydroxymethyl-oxetane.

The 3-hydroxymethyl-oxetanes of the formula (II) are known or can be prepared in a simple fashion by known methods (cf. Houben-Weyl "Methoden der organischen Chemie" [Methods of Organic Chemistry], 4th edition, vol. VI/3, page 493 ff, Georg Thieme Verlag, Stuttgart 1965). Thus, 3-hydroxymethyl-oxetanes of the formula (II) can be obtained, for example, by cleaving carbon dioxide from the appropriate cyclic carbonates.

When carrying out the process according to the invention, suitable catalysts are all conventional palladium and platinum catalysts, and also their mixtures. The catalysts can additionally be combined with activators or mixtures of different activators. Suitable activators here are preferably lead, bismuth, lead compounds and bismuth compounds, and also their mixtures.

When carrying out the process according to the invention, the platinum or palladium, or mixtures which contain these metals, to be used as catalyst can be employed in a conventional fashion. Thus, the substances can be added in elemental form, for example as so-called platinum or palladium black, if appropriate in combination with other platinum-group metals, or alternatively in the form of compounds, such as, for example, the oxides.

The platinum or the palladium can alternatively be applied to a support. Suitable supports are, for example, activated charcoal, graphite, kieselguhr, silica gel, spinels, aluminum oxide, asbestos, calcium carbonate, barium sulphate or alternatively organic support materials.

Activated charcoals, for example so-called medicinal charcoals or activated charcoals produced from wood, as are often used for decolorization purposes, are preferably employed as support material.

The platinum and/or palladium content of the supported catalysts can be varied within a relatively wide range. In general, supported catalysts are used in which the content of these metals is between 0.01 and 20% by weight, preferably between 0.1 and 15% by weight.

The amounts in which the platinum and/or palladium catalysts are employed can also be varied within a relatively wide range. The amounts depend, inter alia, on the desired oxidation rate. In general, the amount of catalyst is selected so that between 0.01 and 20 g, preferably between 0.05 and 10 g, of platinum and/or palladium are present per mole of 3-hydroxymethyl-oxetane of the formula (II) in the reaction mixture.

When carrying out the process according to the invention, it is also possible to employ a combination of platinum and palladium as catalyst.

The activity and/or selectivity of the platinum catalysts is considerably increased in the process according to the invention by the presence as activator of lead and/or of bismuth and/or their compounds.

Even without addition of the abovementioned activators, palladium catalysts have such a surprisingly high activity and selectivity that, when using them, the addition of the abovementioned activators can sometimes be dispensed with.

The addition of the abovementioned activators also has a positive effect on the reusability of the catalysts.

The amounts in which the activators are employed, if appropriate, when carrying out the process according to the invention may be varied within a relatively wide range. The activator action is noticeable at added amounts as small as $5 \times 10^{-6}$ mole of metal or metal compound per mole of 3-hydroxymethyl-oxetane. 0.1 mole or more of activator may also be employed per mole of 3-hydroxymethyl-oxetane, but these greater added amounts do not generally offer an advantage. The activators are conventionally added in amounts from about $1 \times 10^{-5}$ to $1 \times 10^{-1}$ mole, preferably $2 \times 10^{-5}$ to $2 \times 10^{-2}$ mole, per mole of the 3-hydroxymethyl-oxetane to be oxidized.

The metals to be used, if appropriate, as activators when carrying out the process according to the invention may be employed in elemental form and/or in the form of their compounds, for example as oxides, hydroxides, hydrated oxides or oxo acids, or as salts of hydrogen acids, such as chlorides, bromides, iodides, sulphides, selenides and tellurides, or as salts of inorganic oxo acids, such as nitrates, nitrites, phosphites, phosphates, arsenites, arsenates, antimonites, antimonates, bismuthates, stannates, plumbates, selenites, selenates, tellurites, tellurates or borates, or as salts of oxo acids which originate from transition metals, such as vanadates, niobates, tantalates, chromates, molybdates, wolframates or permanganates, or as salts of organic aliphatic or aromatic acids, such as formates, acetates, propionates, benzoates, salicylates, lactates, mandelates, glyoxylates, oxetane-carboxylates, citrates or phenolates, or as complex compounds or as organometallic compound.

The activators may in each case be soluble, partially soluble or insoluble in the reaction mixture.

It is also possible to employ the activators in the process according to the invention in combination with other elements or compounds which are not claimed as activator.

The activators to be employed, if appropriate, when carrying out the process according to the invention may exist in different or in mixed valency states. Changes in valency may also occur during the reaction. If the activators are not already added as oxides and/or hydroxides, it is possible that they are totally or partially converted to these in alkaline medium. After the reaction, the platinum and/or palladium catalyst, with the activator (if this has remained undissolved), can be filtered off and used for further oxidation reactions. Losses of platinum or palladium catalyst and/or of activator should be replaced, if necessary.

The activator can be added to the reaction components as a solid, preferably in finely divided form, or in dissolved form. The activator can also be added as early as during the preparation of the platinum or palladium catalyst, or the platinum or palladium catalyst can be impregnated with the activator. The activator can also serve as support material for the platinum metal.

The oxidation by the process according to the invention is carried out in aqueous alkaline medium at a pH $>7$. The appropriate pH is set by addition of alkalis. Suitable alkalis are compounds of the alkali metals and/or alkaline earth metals, such as the hydroxides, carbonates, bicarbonates, phosphates and borates. The hydroxides and/or carbonates of sodium and/or potassium are preferably employed as alkali.

Since 1 mole of alkali ($OH^\ominus$) is consumed per mole of acid formed during the process according to the invention, the amount of alkali to be employed is about 1 mole of alkali per mole of 3-hydroxymethyl-oxetane. In general, about 1 to 1.5 moles of alkali are employed per mole of 3-hydroxymethyl-oxetane.

Higher ratios can be used, but usually bring no significant advantages. If it is desired that only part of the 3-hydroxymethyl-oxetane employed is oxidized to oxetane-3-carboxylic acid, correspondingly less alkali may also be employed.

The alkali may be added to the reaction mixture all at once at the beginning of the reaction, or alternatively in batches or continuously during the reaction.

The 3-hydroxymethyl-oxetanes are preferably oxidized in aqueous solution. However, other inert organic substances, for example solvents, such as tert.-butanol, acetone, dioxane and/or toluene may also be present. The 3-hydroxymethyl-oxetanes are generally employed in the form of a 2 to 40% strength solution. Which concentration is expedient depends, inter alia, on the desired reaction rate. The latter decreases gradually at relatively high 3-hydroxymethyl-oxetane concentrations. It is also possible to oxidize mixtures of different 3-hydroxymethyl-oxetanes.

The reaction temperatures may be varied within a relatively wide range when carrying out the process according to the invention. Thus, the reaction temperature may be between the solidification point and the boiling point of the reactin mixture. The reaction temperature to be used in an individual case depends, inter alia, on the catalyst system, and the amount of catalyst, the alkali concentration, the substance properties of the educts and products, and on the technical conditions, such as, for example, the desired reaction rate or heat dissipation. In general, the process is carried out at temperatures between 0° C. and the boiling point of the reaction mixture, preferably between 40° C. and 100° C.

Any sequence can be used for mixing together the platinum and/or palladium catalyst, and, if appropriate, activator, aqueous alkali and 3-hydroxymethyl-oxetane. Thus, the platinum and/or palladium catalyst, and, if appropriate, activator, can be added to the mixture or solution of aqueous alkali and 3-hydroxymethyl-oxetane. Alternatively, the mixture of aqueous alkali and 3-hydroxymethyl-oxetane can be added to the platinum and/or palladium catalyst, and, if appropriate, activator. Finally, it is also possible to add the 3-hydroxymethyl-oxetane, together with the remaining alkali, to the platinum and/or palladium catalyst, part of the aqueous alkali, and, if appropriate, activator. Furthermore, it is possible to add the activator to the mixture of the other components.

In general, the process according to the invention is carried out in such a fashion that oxygen or oxygen-containing gases, such as air, are brought into intimate contact with the reaction mixture, which contains aqueous alkali, the platinum and/or palladium catalyst, if appropriate activator, and 3-hydroxymethyl-oxetane. The catalyst need not be present in the reaction mixture suspended as a powder, but can instead be arranged in granular form as a fixed bed through which the other components flow.

When carrying out the process according to the invention, the pressure may be varied within a relatively wide range. In general, the process is carried out at pressures between 0.5 and 10 bar. The oxidation is preferably carried out at atmospheric pressure.

The course of the reaction can be followed by measuring the amount of oxygen taken up. The reaction is terminated when the amount of oxygen which is theoretically necessary for the preparation of the appropriate oxetane-3-carboxylic acid has been taken up. In general, the oxygen take-up ceases of its own accord at this stage, or slows down markedly.

When carrying out the process according to the invention, the reaction mixture is worked up by conventional methods. In general, a procedure is followed in which the catalyst and, if appropriate, any undissolved activator present, is separated off, for example by filtration. The alkali metal salt solutions of the oxetane-3-carboxylic acids obtained can be further used as such, if appropriate after prior concentration by evaporation. The alkali metal salt solutions of the oxetane-3-carboxylic acids can alternatively be evaporated completely, that is to say to dryness, and the salt residue remaining can be further used. If the free oxetane-3-carboxylic acids are to be prepared, a procedure is generally followed in which the reaction mixture remaining, if appropriate after prior concentration under reduced pressure, is acidified using dilute mineral acid, then extracted with an organic solvent which is sparingly soluble in water, and the organic phase, if appropriate after prior drying, is concentrated. Hydrochloric acid, sulphuric acid or phosphoric acid may preferably be employed here as mineral acids. Suitable organic solvents for the extraction are preferably ethers, such as diethyl ether and diisopropyl ether, furthermore ketones, such as methyl isobutyl ketone, and, in addition, optionally halogenated aliphatic or aromatic hydrocarbons, such as methylene chloride, chloroform, tetrachloromethane or toluene. It is also possible to liberate, on a cation exchanger, the respective oxetane-3-carboxylic acid from the aqueous alkali metal salt solutions produced initially, and to isolate them by gentle evaporation of the aqueous solution. If the conversion of the 3-hydroxymethyl-oxetane used is incomplete, this can be removed before acidification by extraction of the aqueous alkali metal salt solution with an organic solvent which is sparingly soluble in water, recovered and, if appropriate, re-employed as starting material.

The oxetane-3-carboxylic acids which can be prepared by the process according to the invention are valuable intermediates for the preparation of other substances. Thus, the oxetane-3-carboxylic acids of the formula (I) may be employed for the synthesis of polyaddition products (German Published Specification No. 1,907,117).

In addition, the oxetane-3-carboxylic acids of the formula (I), or the salts thereof, can also be converted into 2,2-bis-chloromethyl-alkanecarboxylic acid chlorides. Thus, 2,2-bischloromethyl-alkanecarboxylic acid chlorides of the formula

in which R has the abovementioned meaning, are obtained by reacting oxetane-3-carboxylic acids of the formula

in which R has the abovementioned meaning, or salts thereof, with inorganic acid chlorides, if appropriate in the presence of a catalyst and if appropriate in the presence of a diluent, at temperatures between 0° C. and the boiling point of the reaction mixture.

If 3-methyl-oxetane-3-carboxylic acid is used as starting material, thionyl chloride as acid chloride and dimethyl formamide (=DMF) as catalyst, then the course of the above process may be illustrated by the following equation:

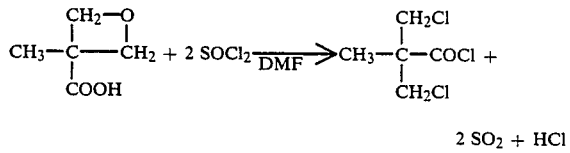

2 SO$_2$ + HCl

In the abovementioned synthesis of 2,2-bis-chloromethyl-alkanecarboxylic acid chlorides of the formula (III), the oxetane-3-carboxylic acids of the formula (I), or alternatively the salts thereof, are suitable as starting materials. As salts here, alkali metal or alkaline earth metal salts, such as sodium, potassium, magnesium or calcium salts, made be employed. The salts of oxetane-3-carboxylic acids of the formula (I) can be prepared by conventional salt-formation reactions. They are produced in the synthesis of oxetane-3-carboxylic acids of the formula (I) by the process according to the invention and, after prior isolation, can be used for the further reaction.

Suitable inorganic acid chlorides in the preparation of the compounds of the formula (III) by the above process are all conventional inorganic acid chlorides. Thionyl chloride, phosphorus trichloride or phosphorus pentachloride may preferably be used.

All those compounds which are also known to catalyze the reaction of carboxylic acids and their salts with inorganic acid chlorides to form carboxylic acid chlorides (cf. Houben-Weyl, "Methoden der organischen Chemie" (Methods of Organic Chemistry), Georg-Thieme-Verlag, vol. VIII, pages 463 ff., Stuttgart 1952, and vol. E5, pages 593 ff (1985)) may be used as catalysts in the preparation of the compounds of the formula (III) by the above process. Basic nitrogen compounds, such as tertiary amines and acid amides, may preferably be used. Pyridine and dimethyl-formamide may be mentioned as examples.

When carrying out the above process for the preparation of the compounds of the formula (III), the reaction temperatures may be varied within a relatively wide range. In general, the process is carried out at temperatures between 20° C. and the boiling point of the reaction mixture.

All conventional inert organic solvents may be used as diluents when carrying out the above process for the preparation of the compounds of the formula (III). Preferably suitable are aliphatic and aromatic, optionally chlorinated hydrocarbons, and also phosphoroxy chloride and carbon disulphide.

When carrying out the above process for the preparation of compounds of the formula (III), a procedure is generally followed in which the oxetane-3-carboxylic acids, or salts thereof, are reacted with a stoichiometric amount, or alternatively with an excess, of inorganic acid chlorides, and if appropriate in the presence of a catalyst. The stoichiometric excess of inorganic acid chlorides here can be 5 to 300%. The catalyst is generally added in amounts from 0.1 to 20% by weight, relative to the oxetane-3-carboxylic acids, or metal salts thereof, employed.

In the above process, the reaction mixture is heated until the reaction is complete, according to the heat and/or gas evolution. For better reaction control, the reaction can alternatively be carried out in the presence of an inert solvent. In general, the reaction mixture is heated to the reflux temperature and maintained at this temperature until the reaction is complete. The course of the reaction and the end of the reaction can be determined in a simple fashion by conventional methods, for example by gas chromatography.

In the above process for the preparation of the compounds of the formula (III), the reaction mixture is worked up by conventional methods. In general, a procedure is followed in which the reaction mixture is subjected to a distillation. Unreacted inorganic acid chloride is collected separately during this and can be used for a further reaction. The distillation should be carried out, if appropriate, in vacuo or by incorporating a column.

The 2,2-bis-chloromethyl-alkanecarboxylic acids of the formula (III) can be used as starting materials for the preparation of herbicidally active triazinone derivatives or for the synthesis of fungicidally active triazolyl derivatives.

For example, 2,2-bis-chloropivaloyl chloride, if appropriate after prior exchange of the chlorine atoms by fluorine atoms, can be converted, by reaction with trimethylsilyl cyanide, into the corresponding halogenopivaloyl cyanides, which can be converted to 1,2,4-triazin-5-one derivatives by known methods (German Published Specification No. 3,037,300).

Furthermore, for example, 2,2-bis-chloropivaloyl chloride can be converted, by treatment with potassium fluoride, into 2,2-bis-fluoropivaloyl fluoride, which reacts with magnesium monoethyl malonate to form 2,2-bis-fluoromethylbutan-3-one. The latter compound reacts with bromine to form 2,2-bis-fluoromethyl-4-bromo-butan-3-one, which, on reaction with 1,2,4-triazole, yields 2,2-bis-fluoromethyl-4-(1,2,4-triazol-1-yl)-butan-3-one. This can be converted into 2,2-bis-fluoromethyl-5-cyclohexyl-4-(1,2,4-triazol-1-yl)-pentan-3-ol by reaction with cyclohexylmethyl bromide and reduction of the product produced initially using sodium borohydride (German Published Specification No. 3,326,875, German Published Specification No. 2,951,163 and Japanese Published Specification No. 61,572 (1985)). The reactions mentioned may be represented by the following equation:

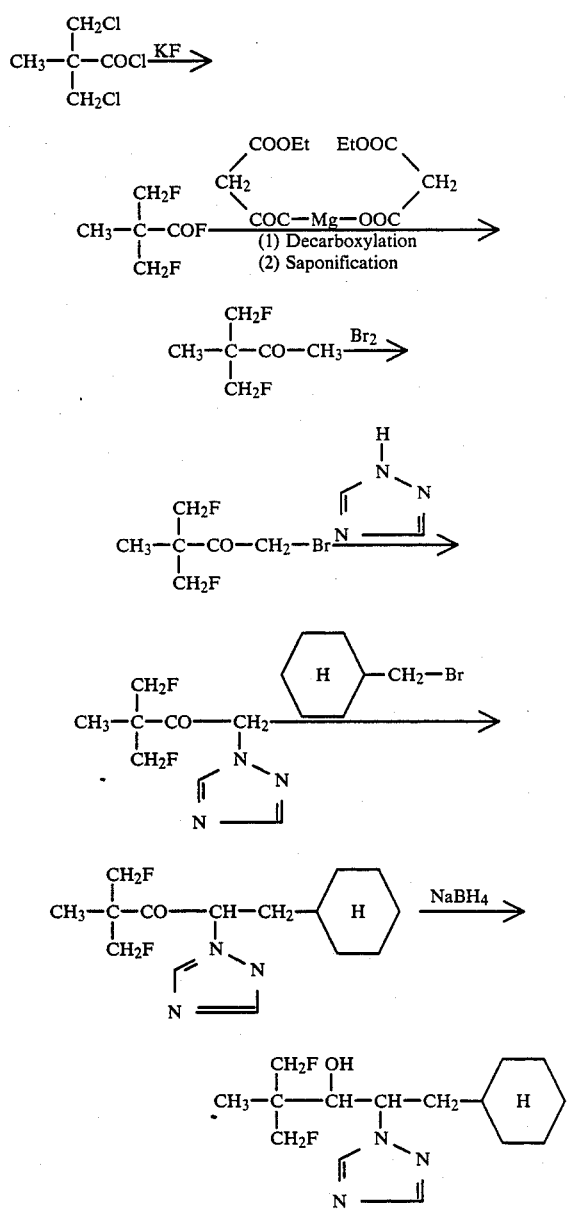

The execution of the process according to the invention is illustrated by the following examples.

EXAMPLE 1

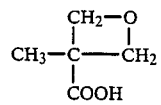

A solution of 20.4 g (0.2 mol) of 3-methyl-3-hydroxymethyl-oxetane in 100 ml (0.22 mol) of 2.2M aqueous sodium hydroxide solution, 1 g of activated charcoal containing 5% by weight of palladium, and 0.030 g of $Bi(NO_3)_3.5H_2O$ are introduced into a reaction vessel which is provided with a stirrer, internal thermometer and gas inlet and the temperature of which is controlled by a heating mantle.

After expelling the air from the reaction vessel using oxygen, the stirrer is switched on and the reaction mixture is heated to 80° C. At this temperature, oxygen under atmospheric pressure is introduced into the mixture. After 3 hours, 0.2 mol of oxygen has been taken up and the reaction ceases.

After filtering off the catalyst and washing with 20 ml of water, the filtrate is acidified to pH 1 using 50% strength sulphuric acid, and is extracted with 2×50 ml of methyl isobutyl ketone. After stripping the methyl isobutyl ketone at 60° C. in vacuo, 24 g of 3-methyl oxetane-3-carboxylic acid which contains, according to a gas chromatogram, 3 to 4% of methyl isobutyl ketone, but otherwise no further impurities, remain as residue. The yield accordingly works out at 99% of theory. M.p. 58°–60° C. (after recrystallization from ligroin).

The catalyst which is filtered off can be reused in the next batch.

EXAMPLE 2

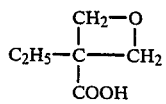

The procedure as in Example 1 is carried out, but with the difference that 11.6 g (0.1 mol) of 3-ethyl-3-hydroxymethyl-oxetane is dissolved in 100 ml of 1.2M aqueous sodium hydroxide solution and, after addition of 1 g of activated charcoal containing 5% by weight of palladium and 30 mg of $Bi(NO_3)_3.5H_2O$, is oxidized at 80° C. using oxygen at atmospheric pressure. After 90 minutes, 0.1 mol of oxygen has been taken up and the reaction ceases.

After filtering off the catalyst, extraction of the filtrate, adjusted to pH 1 using 50% strength sulphuric acid, with diethyl ether affords 12.9 g of a product which, according to a gas chromatogram, is 99.7% 3-ethyloxetane-3-carboxylic acid. The yield accordingly works out at 98.9% of theory. M.p. 25° C.

EXAMPLE 3

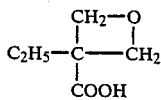

The method given in Example 2 is followed, but without addition of $Bi(NO_3)_3.5H_2O$. After 90 minutes, 0.1 mol of oxygen has been taken up. 12.7 g of a product are obtained which, according to a gas chromatogram, is 99.3% 3-ethyl-oxetane-3-carboxylic acid. The yield accordingly works out at 97% of theory.

EXAMPLE 4

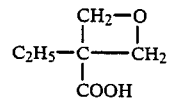

The procedure as in Example 1 is carried out, but with the difference that 34.8 g (0.3 mol) of 3-ethyl-3-hydroxymethyl-oxetane are dissolved in 150 ml of 2.2M aqueous sodium hydroxide solution and, after addition of 1.5 g of activated charcoal containing 5% by weight of palladium, are oxidized at 80° C. using oxygen under atmospheric pressure until the take-up of oxygen ceases. The stirrer is then switched off, the catalyst is allowed to settle, and the supernatant alkaline solution is separated by suction from the catalyst, apart from a small residue, through a tube which is provided with a frit on the end.

The aqueous alkaline solution removed by suction is extracted with methylene chloride in order to remove unreacted 3-ethyl-3-hydroxymethyl-oxetane, then acidified to pH 1 using 50% strength sulphuric acid, and re-extracted with methylene chloride in order to obtain the 3-ethyl-oxetane-3-carboxylic acid.

A further 34.8 g (0.3 mol) of 3-ethyl-3-hydroxymethyl-oxetane and 150 ml of 2.2M aqueous sodium hydroxide are subsequently added to the catalyst remaining in the reaction vessel. The oxidation at 80° C. and the work-up are then carried out again as described above.

The entire process is subsequently repeated again. The catalyst is employed in this fashion a total of 4 times. The experiment is then terminated.

The times until cessation of oxygen take-up are 180, 210, 300 and 510 minutes for the first, second, third and fourth use respectively of the catalyst.

A total of 146.3 g of a product are isolated which, according to a gas chromatogram, is 99.5% 3-ethyl-oxetane-3-carboxylic acid. The total yield accordingly works out at 93.3% of theory.

EXAMPLE 5

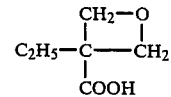

The procedure as in Example 4 is carried out, but with the difference that 50 mg of $Bi(NO_3)_3.5H_2O$ are added as activator in the case of the first use of the catalyst and 25 mg of $Bi(NO_3)_3.5H_2O$ are added in the case of each further use of the catalyst.

In total, the catalyst is used 18× in this fashion. The experiment is then terminated.

The times until cessation of take-up of oxygen are

| | |
|---|---|
| 1st use of the catalyst | 180 minutes |
| 4th use of the catalyst | 210 |
| 8th use of the catalyst | 270 |
| 12th use of the catalyst | 300 |

When a total of 18×34.8=624.4 g of 3-ethyl-3-hydroxymethyl-oxetane are used, a total of 696.1 g of 98.5% purity 3-ethyl-oxetane-3-carboxylic acid are obtained. This corresponds to a yield of 97.7% of theory.

Comparison with Example 4 shows the positive effect of the activator on the maintenance of the activity of the catalyst.

EXAMPLE 6

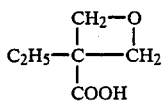

The procedure as in Example 2 is carried out, but at 50° C. After 6 hours, 0.097 mol of oxygen has been taken up, and the take-up of oxygen has not yet ceased completely. 12.5 g of a product are obtained which, according to a gas chromatogram, is 97.8% 3-ethyl-oxetane-3-carboxylic acid. The yield accordingly works out at 94% of theory.

EXAMPLE 7

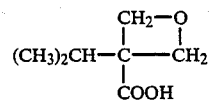

The procedure as in Example 1 is carried out, but with a difference that 13 g (0.1 mol) of 3-isopropyl-3-hydroxymethyl-oxetane in 100 ml of 1.2M aqueous sodium hydroxide solution are oxidized in the presence of 1 g of activated charcoal containing 5% by weight of palladium and 30 mg of Bi(NO$_3$)$_3$.5H$_2$O. After 120 minutes, 0.1 mol of oxygen has been taken up, and the take-up of oxygen has ceased.

After filtering off the catalyst, acidifying the filtrate to pH 1 and extracting with diethyl ether, 14.1 g of a product which is 94.5% 3-isopropyl-oxetane-3-carboxylic acid and 3.3% 3-isopropyl-3-hydroxymethyl-oxetane remain after concentration of the organic phase under reduced pressure. The yield (selectivity) accordingly works out at 96% of theory, relative to the unreacted starting material. M.p. 52°–54° C.

EXAMPLES 8 TO 10

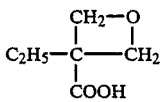

The procedure as in Example 1 is carried out, but with the difference that 11.6 g (0.1 mol) of 3-ethyl-3-hydroxymethyl-oxetane are dissolved in 100 mols of 1.2N aqueous sodium hydroxide solution and, after addition of 1 g of activated charcoal containing 1% by weight of platinum, are oxidized at 80° C. using oxygen under atmospheric pressure in the absence (comparison example) or presence of 30 mg of Bi(NO$_3$)$_3$.5H$_2$O (Example 9) or 0.5 ml of 1M Pb(NO$_3$)$_2$ solution (Example 10) as activator.

Work-up is effected, after filtering off the catalyst under suction, by acidifying to pH 1 and extracting with diethyl ether. The results achieved are listed in the following Table 1.

TABLE 1

The influence of lead and bismuth on the oxidation of 3-ethyl-3-hydroxymethyl-oxetane at 80° C.

| Example | Activator | Take-up of O$_2$ mol of O$_2$ mol of oxetane | time required hours | Yield in % of theory |
|---|---|---|---|---|
| 8+ | none | 0.05 | 7 | <5% |
| 9 | Bi(NO$_3$)$_3$ | 1.00 | 1.5 | 97.3 |
| 10 | Pb(NO$_3$)$_3$ | 1.00 | 1.0 | 98.5 |

+for comparison

EXAMPLE 11

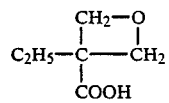

The procedure as in Example 10 is carried, but at an oxidation temperature of 50° C. After 2 hours, 0.9 mol of oxygen has been taken up per mol of 3-ethyl-3-hydroxymethyl-oxetane. After working up, 3-ethyl-oxetane-3-carboxylic acid is obtained in a yield of 86.2% of theory.

EXAMPLE 12

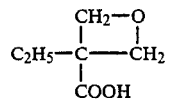

The procedure as in Example 10 is carried out, but at an oxidation temperature of 40° C. After 2 hours, 0.8 mol of oxygen have been taken up per mol of 3-ethyl-3-hydroxymethyl-oxetane. After working up, 3-ethyl-oxetane-3-carboxylic acid is obtained in a yield of 86.2% of theory.

Preparation of 2,2-bis-chloromethyl-alkanecarboxylic acid chlorides, starting from oxetane-3-carboxylic acids:

EXAMPLE 13

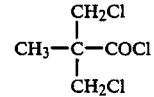

A mixture of 11.6 g (0.1 mol) of 3-methyl-oxetane-3-carboxylic acid, 35.7 g (0.3 mol) of thionyl chloride and 0.2 ml of dimethylformamide is heated slowly to the reflux temperature (about 120° C.), gas being evolved during the heating. The mixture is then stirred for 5 hours at this temperature. The investigation of a sample by gas chromatography indicates that the 3-methyl-oxetane-carboxylic acid employed has reacted completely. Excess thionyl chloride is subsequently removed by distillation over a distillation bridge. The main fraction is removed from the residue remaining by distillation at a pressure of 10 mbar at 70°–90° C. 15.5 g of a product are obtained which, according to a gas chromatogram, -continued

| 18th use of the catalyst | 420 | is 96.1% 2,2-bis-chloromethyl-propanecarboxylic acid chloride.

EXAMPLE 14

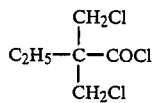

476 g (4 mol) of thionyl chloride are added dropwise to a mixture of 130 g (1 mol) of 3-ethyl-oxetane-3-carboxylic acid and 1 ml of dimethylformamide. The mixture is then heated to the reflux temperature in such a fashion that a constant stream of waste gas is produced. The mixture is subsequently stirred at the reflux temperature. After a total of 32 hours, the mixture is distilled over a bridge. In the boiling range from 95° to 120° C. at a pressure of 10 mbar, 166.6 g (0.82 mol) of 2,2-bis-chloromethyl-butanecarboxylic acid chloride are obtained which solidifies on standing at room temperature. M.p. 38°–40° C.

It will be understood that the specification and examples are illustrative but not limitative of the present invention and that other embodiments within the spirit and scope of the invention will suggest themselves to those skilled in the art.

What is claimed is:

1. A process for the preparation of an oxetane-3-carboxylic acid of the formula

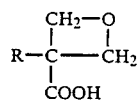

in which R represents hydrogen, alkyl having 1 to 12 carbon atoms, cycloalkyl having 3 to 8 carbon atoms, or phenyl which is optionally substituted by at least one of halogen and alkyl having 1 to 4 carbon atoms, comprising reacting a 3-hydroxymethyl-oxetane of the formula

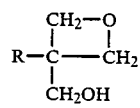

with oxygen in an aqueous solution of an alkali metal compound or an alkaline earth metal compound at a temperature between about 40° C. and 100° C. in the presence of a palladium and/or platinum catalyst and in the presence of an activator selected from lead, bismuth, a lead compound, a bismuth compound or a mixture thereof.

2. A process according to claim 1, wherein the platinum and/or palladium catalyst is employed in the form of a supported catalyst.

3. A process according to claim 2, wherein the catalyst support is activated charcoal.

4. A process according to claim 1, wherein air is used as the oxygen source.

5. A process according to claim 1, including the further step of acidifying the reaction mass.

6. A process according to claim 1, in which R is methyl.

7. A process according to claim 1, in which R is ethyl.

8. A process according to claim 1, in which R is isopropyl.

* * * * *

UNITED STATES PATENT AND TRADEMARK OFFICE
CERTIFICATE OF CORRECTION

PATENT NO. : 4,824,975

DATED : April 25, 1989

INVENTOR(S) : Fiege et al

It is certified that error appears in the above-identified patent and that said Letters Patent is hereby corrected as shown below:

Col. 14, line 10          Delete "4" and substitute ---6---

Signed and Sealed this

Twenty-fourth Day of July, 1990

Attest:

HARRY F. MANBECK, JR.

*Attesting Officer*          *Commissioner of Patents and Trademarks*